(12) United States Patent
Barratt et al.

(10) Patent No.: US 7,550,647 B2
(45) Date of Patent: Jun. 23, 2009

(54) TRANSFECTED SHRIMP AS PRODUCTION SYSTEMS FOR THERAPEUTIC PROTEINS

(75) Inventors: Ruth Barratt, Gaithersburg, MD (US); F. C. Thomas Allnutt, Glenwood, MD (US); Robert Bullis, Ellicott City, MD (US); David J. Kyle, Catonsville, MD (US)

(73) Assignee: Advanced BioNutrition, Columbia, MD (US)

( * ) Notice: Subject to any disclaimer, the term of this patent is extended or adjusted under 35 U.S.C. 154(b) by 198 days.

(21) Appl. No.: 10/778,175

(22) Filed: Feb. 17, 2004

(65) Prior Publication Data

US 2004/0177392 A1    Sep. 9, 2004

Related U.S. Application Data

(63) Continuation-in-part of application No. PCT/US02/29081, filed on Sep. 13, 2002.

(60) Provisional application No. 60/318,867, filed on Sep. 14, 2001, provisional application No. 60/473,928, filed on May 29, 2003.

(51) Int. Cl.
   *A01K 67/00*   (2006.01)
   *A01K 67/033*  (2006.01)

(52) U.S. Cl. ............................................. 800/8; 800/13

(58) Field of Classification Search ........................ None
   See application file for complete search history.

(56) References Cited

U.S. PATENT DOCUMENTS

| 4,141,986 A | 2/1979 | Cassidy |
| 5,202,422 A | 4/1993 | Hiatt |
| 5,681,746 A | 10/1997 | Bodner |
| 5,863,775 A | 1/1999 | Atkinson |
| 2001/0006953 A1 | 7/2001 | Poet |

FOREIGN PATENT DOCUMENTS

| WO | WO91/06320 | | 5/1991 |
| WO | WO 96/40935 | | 12/1996 |
| WO | WO 00/75288 | | 12/2000 |
| WO | WO0109340 | * | 2/2001 |
| WO | WO 03/017780 | | 3/2003 |
| WO | WO 03/024482 | | 3/2003 |

OTHER PUBLICATIONS

Loh. Encyclopedia of Virology. Ed. A. Granoff and R.G. Webster. San Diego: Academic Press. Shrimp Viruses, pp. 1625-1635, 1999.*
Rajendran et al. J Fish Diseases 22, 183-191, 1999.*
Dai H et al. (2003) Construction and characterization of a novel recombinant single-chain variable fragment antibody against White Spot Syndrome Virus from shrimp. J Immunol Methods 279:267-275.
Mayfield S, Franklin S, Lerner R (2003) Expression and assembly of a fully active antibody in algae. Proc Nat Acad Sci USA 100:438-442.
Thomas JM, Klimstra WB, Ryman KD, Heidner HW (2003) Sindbis virus vectors designed to express a foreign protein as a cleavable component of the viral structural polyprotein. J Virol 77:5598-5606.
Chambers TJ et al. (2003) Yellow fever virus/dengue-2 virus and yellow fever virus/dengue-4 virus chimeras: biological characterization, immunogenicity, and protection against dengue encephalitis in the mouse model. J Virol 77:3655-3668.
Tsang WS, et al. (2003) Organization of the shrimp vitellogenin gene: evidence of multiple genes and tissue specific expression by the ovary and hepatopancreas. Gene. 303:99-109 (abstract).
Chen LL et al. (2002) Identification of a nucleocapsid protein (VP35) gene of shrimp white spot syndrome virus and characterization of the motif important for targeting VP35 to the nuclei of transfected insect cells. Virology 293:44-53.
Zasloff M (2002) Antimicrobial peptides of multicellular organisms. Nature 415:389-395.
Niikura M et al. (2002) Chimeric recombinant hepatitis E virus-like particles as an oral vaccine vehicle presenting foreign epitopes. Virology 293:273-280.
Lauth X, Shike H, Burns J, Westerman ME OV, Carlberg JM, Van Olst JC, Nizet V, Taylor SW, Shimizu C, Bulet P. (2002) Discovery and characterization of two isoforms of moronecidin, a novel antimicrobial peptide from hybrid striped bass. J Biol Chem 277:5030-5039.

(Continued)

*Primary Examiner*—Deborah Crouch
*Assistant Examiner*—Marcia S Noble
(74) *Attorney, Agent, or Firm*—Marianne Fuierer; Moore & Van Allen PLLC

(57) ABSTRACT

A crustacean or rotifer is infected with a recombinant infectious virus that expresses a protein exogenous to the virus. The genome of the crustacean or rotifer itself remains unaltered. Crustacean, rotifer, insect, or viral promoters drive the transcription of a gene inserted into the recombinant virus genome, and the virus replicates in the crustacean or rotifer cell cytoplasm. The infected crustacean or rotifer can be provided directly to humans or non-human animals, or, following production and harvest of the crustaceans or rotifers, purified recombinant protein or polypeptide can be provided. Large quantities of biopharmaceuticals can be produced rapidly and inexpensively using this production system.

15 Claims, 1 Drawing Sheet

OTHER PUBLICATIONS

Humphrey B, Huang N, Klasing K (2002) Rice expressing lactoferrin and lysozyme has antibiotic-like properties when fed to chicks. J Nutr 132:1214-1218.

Kim D et al. (2002) Stable Integration and Functional Expression of Flounder Growth Hormone Gene in Transformed Microalga, Chlorella ellipsoidea, Mar. Biotechnol. 4, 63-73.

Yu J., Langridge WH (2001) A plant-based multicomponent vaccine protects mice from enteric diseases. Nat. Biotechnol., vol. 19, pp. 548-552.

Li T, Takeda N, Miyamura T (2001) Oral administration of hepatitis E virus-like particles induces a systemic and mucosal immune response in mice. Vaccine 19:3476-3484.

Lindbo JA, Fitzmaurice WP, della-Cioppa G (2001) Virus-mediated reprogramming of gene expression in plants. Curr Opin Plant Biol 4:181-185.

Shike H, Shimizu C, Klimpel KS, Burns JC (2000) Expression of foreign genes in primary cultured cells of the blue shrimp Penaeus stylirostris. Marine Biol 137:605-612.

Perri S et al. (2000) Replicon vectors derived from Sindbis virus and Semliki forest virus that establish persistent replication in host cells. J Virol 74:9802-9807.

Mayfield S et al. (2000) Expression of antibodies in microalgae. The Scaggs Institute for Chemical Biology Scientific Report 1999-2000, Scripps Research Institute, San Diego.

Ebran N, Julien S, Orange N, Auperin B, Molle G (2000) Isolation and characterization of novel glycoproteins from fish epidermal mucus: correlation between their pore-forming properties and their antibacterial activities. Biochim Biophys Acta 1467:271-280.

Shike H et al. (2000) Infectious hypodermal and hematopoietic necrosis virus of shrimp is related to mosquito brevidensoviruses. Virology 277(1):167-77.

Cregg JM et al. (2000) Recombinant protein expression in pichia pastoris. Molecular Biotechnology 16:23-52.

Cha HJ et al. (1999) Insect Larval Expression Process is Optimized by Generating Fusions with Green Fluorescent Protein. Biotechnology and Bioengineering, vol. 65, pp. 316-324.

Lewis DL et al. (1999) Ectopic gene expression and homeotic transformations in arthropods using recombinant Sindbis viruses. Curr Biol 9:1279-1287.

Que X, Kim D, Alagon A, Hirata K, Shike H, Shimizu c, Gonzalez A, Burns JC, Reed SL (1999) Pantropic retroviral vectors mediate gene transfer and expression in Entamoeba histolytica. Mol Biochem Parasitol 99:237-245.

Schep LJ, Tucker IG, Young G, Ledger R, Butt AG (1999) Controlled release opportunities for oral peptide delivery in aquaculture. J Control Release 59:1-14.

Modelska A., et al. (1998) Immunization against rabies with plant -derived antigen. Proc. Natl., Acad. Sci. USA, vol. 95, pp. 2481-2485.

Arakawa T, Yu J, Chong DK, Hough J, Engen PC, Langridge WH (1998) A plant-based cholera toxi B subunit-insulin fusion protein protects against the development of autoimmune diabetes. Nat Biotechnol 16:934-938.

Yao K, Vakharia VN (1998) Generation of infectious pancreatic necrosis virus from cloned cDNA. J. Virol 72:8913-8920.

Jiang B et al. (1998) Synthesis of rotavirus-like particles in insect cells: comparative and quantitative analysis. Biotechnol Bioeng 60:369-374.

Mason HS, Haq TA, Clements JD, Arntzen CJ (1998) Edible vaccine protects mice against Escherichia coli heat-labile enterotoxin (LT): potatoes expressing a synthetic LT-B gene. Vaccine 16:1336-1343.

Tsoka S et al. (1998) Virus-like particle analysis in yeast homogenate using a laser light-scattering assy. Biotechnology and Bioengineering 63 (Pt 3) 290-297.

Jarvis DL, Kawar ZS, Hollister JR (1998) Engineering N-glycosylation pathways in the baculovirus-insect cell system. Curr Opin Biotechnol 9:528-533 (abstract).

Chan SM, Chen XG, Gu PL (1998) PCR cloning and expression of the molt-inhibiting hormone gene for the crab (Charybdis feriatus). Gene 224:23-33 (abstract).

Gu PL, Chan SM (1998) Cloning of a cDNA encoding a putative molt-inhibiting hormone from the eyestalk of the sand shrimp Metapenaeus ensis. Mol Mar Biol Biotechnol. 7:214-20 (abstract).

Leong JC et al. (1997) Fish vaccine antigens produced or delivered by recombinant DNA technologies. Dev Biol Stand 90:267-277.

Christie KE (1997) Immunization with viral antigens: infectious pancreatic necrosis. Dev Biol Stand 90:191-199 (abstract).

Mason HS, Ball JM, Shi JJ, Jiang X, Estes MK, Arntzen CJ (1996) Expression of Norwalk virus capsid protein in transgenic tobacco and potato and its oral immunogenicity in mice. Proc Natl Acad Sci U S A 93:5335-5340.

Mundt E, Vakharia VN (1996) Synthetic transcripts of double-stranded Birnavirus genome are infectious. Proc Natl Acad Sci U S A 93:11131-11136.

Wickner RB (1996) Double-stranded RNA viruses of Saccharomyces cerevisiae. Microbiol Rev 60:250-265.

Tapay LM, Lu Y, Brock JA, Nadala EC, Jr., Loh PC (1995) Transformation of primary cultures of shrimp (Penaeus stylirostris) lymphoid (oka) organ with Simian virus-40 (T) antigen. Proc Soc Exp Biol Med 209:73-78 (abstract).

Haq TA, Mason HS, Clements JD, Arntzen CJ (1995) Oral immunization with a recombinant bacterial antigen produced in transgenic plants. Science 268:714-716.

Castillo A, Cifuentes V (1994) Presence of double-stranded RNA and virus-like particles in Phaffia rhodozyma. Curr Genet 26:364-368.

Saliki JT et al. (1992) Canine parvovirus empty capsids produced by expression in a baculovirus vector: use in analysis of viral properties and immunication of dogs. J Gen Virol 73 (Pt 2): 369-374 (abstract).

Mayfield S, Kindle K (1990) Stable nuclear transformation of Chlamydomonas reinhardtii by using a C. reinhardtii gene as the selectable marker. Proc Natl Acad Sci U S A 87:2087-2091.

Tuse D (1984) Single-cell protein: current status and future prospects. Crit Rev Food Sci Nutr 19:273-325.

Altmann F, Staudacher E, Wilson IB, Marz L (1999) Insect cells as hosts for the expression of recombinant glycoproteins, Glycoconj. J. 16:109-123.

Sarmasik, A; Jang, In-Kwon; Chun, C.Z.; Lu, J.K.; and Chen, Thomas.; (2001) Transgenic Live-Bearing Fish and Crustaceans Produced by Transforming Immature Gonads with Replication-Defective Pantropic Retroviral Vectors; Marine Biotechnology, V(3) pp. 470-471.

* cited by examiner

TRANSFECTED SHRIMP AS PRODUCTION SYSTEMS FOR THERAPEUTIC PROTEINS

CROSS-REFERENCE TO RELATED APPLICATIONS

This application is a Continuation-In-Part application of PCT/US02/29081, filed Sep. 13, 2002, which claims the benefit of U.S. Provisional Application No. 60/318,867, filed Sep. 14, 2001, the entire disclosures of which are incorporated by reference. This application also claims the benefit of U.S. Provisional Application No. 60/473,928, filed May 29, 2003, the entire disclosure of which is incorporated by reference.

BACKGROUND OF THE INVENTION

1. Field of the Invention

This application is directed to the construction and use of recombinant infectious crustacean and rotifer viruses for the production of peptides and proteins, such as biopharmaceuticals, vaccines, antibodies, enzymes, and hormones, in a crustacean or rotifer.

2. Description of Related Art

The importance of recombinant proteins for modern medical applications and therapy has been pivotal for the rapid advances over the last two decades. Recombinant production methods for bacteria are well developed (Sambrook, Fritsch et al. 1989; Ratledge and Kristiansen 2001). Many proteins are commercially produced in bacterial prokaryotic systems, and have importance in industry and medical science. Recombinant protein production in yeast and other fungi has been extremely well developed both in the laboratory and on a commercial scale (Keranen and Penttila 1995; Archer and Peberdy 1997; Cereghino and Cregg 1999). Due to the requirement for certain types of posttranslational modification for the full and complete function of recombinant proteins in human or animal systems (i.e., glycosylation of the recombinant protein), much of the biopharmaceutical protein production utilizes mammalian cell culture (Ratledge and Kristiansen 2001).

Problems with the production of recombinant proteins using mammalian cell culture (e.g., CHO cells) include the high cost of production and the generally low yield of the recombinant proteins over time, compared to the yields from other single cell systems such as bacteria, yeast, or other fungi. The production of recombinant proteins using insect cells partially overcomes some of these problems, but yields remain relatively low (Goosen 1993).

The production of recombinant proteins in intact insect larvae has provided a potential solution to the high cost of production in insect cell culture (Cha, Dalal et al. 1999). To accomplish this, insect larvae are infected with a modified recombinant virus containing a gene that codes for the expression of a protein of interest. Problems with the insect larval transfection production system include a limited ability to scale up the production of the recombinant proteins, the requirement for purification of the biopharmaceutical, even if it is to be delivered orally, and the fact that the glycosylation pattern of insect-derived biopharmaceuticals is significantly different from that produced by mammalian cell culture. Furthermore, since insects are non-conventional food sources, direct use of their biomass for delivery of recombinant proteins is problematic.

The production of biopharmaceuticals and other recombinant proteins using plant-based systems has been well established (Stoger, Sack et al. 2002). Such a system can be easily scaled up to produce large quantities of the recombinant protein at a relatively low cost. Problems associated with the plant-based expression systems include a long grow-out period, a generally low level of gene expression when transformation is used, a requirement for purification before use even if the product is to be used orally, and a posttranslational modification system that is generally devoid of sialic acid residues (Stoger, Sack et al. 2002).

SUMMARY OF THE INVENTION

The present invention overcomes the deficiencies in the above protein expression systems. The use of crustaceans and rotifers overcomes the scale-up problem associated with insect larval production. For example, large-scale cultivation methods for shrimp allow the production of the biopharmaceutical products or recombinant proteins at a scale and cost even lower than that for a plant based production system. In addition, the use of a crustacean to produce proteins provides a posttranslational modification pattern for the expressed proteins that is more similar to mammalian systems than plants. Indeed, the glycosylation patterns of crustaceans are even more similar to mammalian glycosylation patterns (i.e., terminal sialylation) than those of insects (Compere, Jaspar-Versali et al. 2002). Finally, certain crustacean and rotifer viruses, which are included in this invention, are among the most virulent viral systems known. The White Spot Syndrome Virus (WSSV), for example, can infect and completely destroy an entire population of shrimp in a matter of days.

In a first aspect, the invention provides crustaceans and rotifers infected with a recombinant, infectious virus that resides in the cells of the crustaceans and rotifers without changing their genetic material.

In a second aspect, the invention provides a recombinant, infectious virus capable of infecting and replicating in a crustacean or rotifer cell. The virus includes a nucleic acid sequence comprising a promoter that is active in the crustacean or rotifer, and encodes one or more proteins or peptides that are not native to the virus. These proteins or peptides can be biopharmaceuticals, vaccines, enzymes, hormones, antibodies, and/or structural proteins.

In a third aspect, the invention provides a method of producing a recombinant protein by infecting a crustacean or rotifer with a recombinant, infectious virus that replicates in the crustacean or rotifer cell without altering the host cell genome. The crustacean or rotifer can be infected at a temperature that is permissive for infection, but at which temperature the virus does not injure the cell. The temperature can then be lowered to a temperature that triggers viral replication and recombinant protein expression.

This method can produce a therapeutic protein or peptide by infecting a crustacean or rotifer with a recombinant, infectious virus that encodes the therapeutic protein or peptide. The method can be performed by preparing a cDNA clone, ligating the clone into the viral transformation vector, and infecting the crustacean or rotifer with the recombinant virus.

In a fourth aspect, the invention provides a method of delivering a therapeutic protein or peptide to a human or non-human animal via a crustacean or rotifer infected with a recombinant, infectious virus. The crustacean or rotifer can, e.g., be infected by feeding with edible material comprising the virus. The non-human animals include animals produced in aquaculture and terrestrial agriculture. The crustaceans can be fed directly to the animal, or the virus can first be enriched or purified, following enrichment or purification procedures well known to those familiar with the art (e.g., Scopes 1984; Deutschen 1990). Recombinant proteins produced by the virus can be introduced to a human or non-human animal by feeding, or by means other than feeding, e.g., by transdermal, mucosal (nasal, oral, vaginal, or rectal), or injection routes.

In a fifth aspect, the invention provides a method of producing an antigen in a crustacean or rotifer by infecting the crustacean or rotifer with a recombinant, infectious, DNA or RNA virus that can be partially purified before infecting the crustacean or rotifer.

In a sixth aspect, the invention provides a method of vaccinating a human or non-human animal by infecting a crustacean or rotifer with a recombinant, infectious DNA or RNA virus that provides genetic material that expresses an antigen. The crustacean or rotifer is then provided to the human or non-human animal in an amount sufficient to elicit a protective immune response. Crustaceans suitable for practicing this method include shrimp, *Artemia*, lobster, crayfish, and crab. The invention also provides a method of using such a vaccine by providing it to a human or non-human animal.

In a seventh aspect, the invention provides a method of treating a human or non-human animal by infecting a crustacean or rotifer with a recombinant infectious virus comprising a therapeutic protein peptide, antibody, antibody fragment, virus-like particle, hormone, and/or vaccine, and further comprising a promoter that functions in the crustacean or rotifer to allow expression of the therapeutic protein; and contacting the human or non-human animal with the crustacean or rotifer. The therapeutic can be insulin, and can be delivered by a route chosen from oral, mucosal, transdermal, and injectable. The therapeutic can also inhibit the growth or replication of a bacterium, e.g., Vibrio, or it can inhibit a disease-causing virus, e.g., a Taura or White Spot virus. This method includes treating with a recombinant, infective virus that encodes more than one polypeptide.

DETAILED DESCRIPTION OF THE INVENTION

Definitions

Figure 1:
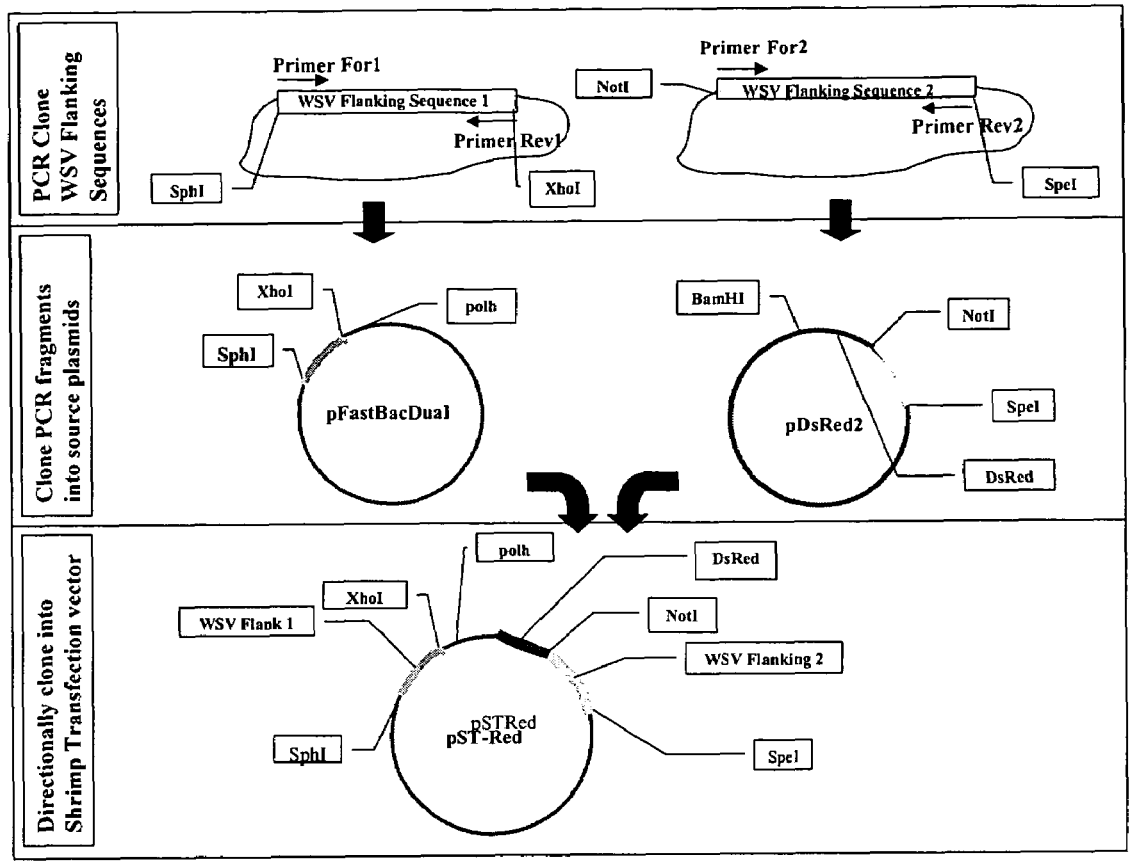
FIG. 1. Production of Recombinant WSSV (rWSSV) With a Viral Promoter Driving Expression of a Selectable Marker. The first half of an identified WSSV flanking region WSV Flanking Sequence 1, or FL1 was amplified to facilitate directional cloning downstream of a reporter gene, DsRed. The WSV was cloned downstream of the DsRed sequence in a pUC plasmid backbone, and transformed in *E. coli*. The second half of the WSSV flanking region (WSV Flanking Sequence 2, or FL2) was amplified, then directionally cloned upstream of the polyhedron (polh) promoter of the commercially available pFastBacDual plasmid (Invitrogen). The DsRed/FL2 sequence was excised from the pUC plasmid backbone. The final construct is shown in FIG. 1 (see Example 1).

A "recombinant virus" is any virus that is formed by joining the DNA of a virus with DNA of an exogenous source.

An "infectious virus" is any virus capable of being transmitted by infection, with or without the virus coming in contact with the target of infection.

A "retrovirus" is any virus in the family Retroviridae that comprises RNA as its nucleic acid, and uses the enzyme reverse transcriptase to copy its genome into the DNA of a host cell chromosome. A retrovirus can act as an "integrative" virus, as used herein.

"Genome" is defined herein as the total set of genes carried by an individual or a cell present in a cell of a host organism.

"Transfection" is defined herein as the infection of a host cell with an infectious virus, e.g., an infectious recombinant virus, which will recruit the biosynthetic machinery of the host cell to both produce more virions and the recombinant protein of interest, without changing or modifying the genome of the host organism.

"Transformation" is defined herein as the direct genetic modification of a host organism's genome that is transferred to daughter cells when the cell divides. This genetic modification can be made by the insertion of a gene of interest into the host cell's DNA either by introducing naked DNA or retroviral DNA. The gene may or may not be expressed by that host organism.

A "promoter" is a sequence of DNA that can initiate the transcription of a gene and is typically placed in a position upstream from the start codon of the Open Reading Frame (ORF) of the gene to be expressed. Promoters can be naturally occurring or engineered sequences. Promoters vary in strength. Promoter sequences at which RNA polymerase initiates transcription at a high frequency are classified as "strong," and those with a low frequency of initiation, as "weak."

An "operon" is a group of genes that is transcribed into a single RNA molecule.

The terms "polypeptide," "peptide," and "protein," used interchangeably herein, refer to a polymeric form of amino acids of any length.

"Fusion proteins" are proteins or polypeptides that contain amino acids from more than one source. They include polypeptides with changed or inserted amino acids, and polypeptides fused to one or more detectable reporter proteins. They also include, but are not limited to, fusion proteins with a heterologous amino acid sequence, fusion proteins with or without N-terminal methionine residues, and immunologically tagged proteins.

A "purified" recombinant infectious virus is one that is substantially free of the substances with which it is associated in an expression system.

A "crustacean" is any organism of the class Crustacea.

A "rotifer" is any of a class of minute, usually microscopic, multi-cellular aquatic invertebrate animals with the anterior end having the characteristic of a retractile disk, bearing circles of strong cilia that can give the appearance of rapidly revolving wheels. Rotifers are used as a source of live feed for aquatic animals during their early larval stages.

An "insect" is any organism of the class Insecta.

An "antigen" is a molecule that can induce an immune response.

A "pharmaceutically acceptable excipient" is an inert substance used as a diluent or vehicle for a drug, which is suitable for use in humans or non-human animals.

DETAILED DESCRIPTION OF VARIOUS EMBODIMENTS OF THE INVENTION

The inventors have discovered that using crustacean, rotifer, insect, or invertebrate viral promoters in a transfection system involving crustacean or rotifer viruses, one can produce large quantities of recombinant proteins at a much lower cost than possible in a mammalian system.

In general, the present invention harnesses the virulence of crustacean and rotifer viruses such as, but not limited to, WSSV, Taura Syndrome Virus (TSV), and Infectious Hypodermal and Hematopoietic Necrosis Virus (IHHNV), to produce biopharmaceuticals, vaccines, and other recombinant proteins, by transfection rather than by direct genetic modification of the host organism's DNA. Burns and Shike (PCT Application WO 00/75288 A1) have described the use of recombinant (integrative) retroviral DNA vectors to transform host DNA in various invertebrate systems including crustaceans. This approach involves a permanent and specific alteration of the host genome by the retrovirus and, as a consequence, the host organism would be considered a genetically modified organism (GMO). Producing recombinant proteins in this way has several disadvantages, including sociological and environmental concerns over producing GMOs (e.g., escape of GMOs into wild populations), as well as a generally low yield and the requirement to have specific genetically engineered lines of animals to produce the biopharmaceutical of interest. The present invention overcomes these problems by the use of transfection (i.e., a process that does not alter the genetic composition of the host animal), resulting in a rapid infection and higher level of expression compared to a retrovirus.

Furthermore, the use of WSSV in particular embodiments of the present invention has a particular advantage in that the virulence of the virus can be controlled by temperature. The WSSV will infect, but is not lethal, at temperatures above about 31° C. (Vidal, Granja et al. 2001). Once the temperature is lowered to about or below 28° C., the virus appears to switch on a massive production capacity that will kill the host very quickly. This "temperature trigger" can be used to synchronize the production of the protein of interest and allow the maximum efficiency for production. Other viruses, such as TSV, can also be used in this fashion, as they too exhibit a similar "temperature trigger" (Montgomery-Brock, Shimojo et al. 2002).

The present invention, therefore, provides a method to rapidly and inexpensively produce large quantities of biopharmaceuticals using a rotifer or crustacean, such as a shrimp, as the production system. Such a biopharmaceutical can be delivered orally by ingestion of the rotifer or crustacean itself (they are considered a conventional food source), or after purification of the biopharmaceutical following production and harvest of the crustacean or rotifer. In this way, the disclosed invention overcomes many of the difficulties with the production of biopharmaceuticals and recombinant proteins in other known systems.

The invention is provided by one or more of the following embodiments. One embodiment of the invention includes a composition comprising a crustacean or rotifer, or parts thereof, which is infected by a recombinant infectious virus comprising a promoter that functions in that crustacean or rotifer to allow expression of a gene encoding a polypeptide that is not native to the virus. The recombinant virus contains a gene coding for the protein to be expressed downstream from a promoter that is active in the host; the promoter can be exogenous. Any promoter active in a crustacean or a rotifer can be used in this invention. The promoter can be exogenous, and more than one promoter can be present in the recombinant virus. The promoter can also be a viral promoter or an insect promoter. The promoter can be an invertebrate viral promoter, such as, but not limited to, the P2 or P61 promoters from the IHHNV shrimp virus (Shike, Dhar et al. 2000). The promoter can also be a promoter from invertebrates, such as, but not limited to, the hemocyanin or molt-inhibiting promoters in shrimp. Other exemplary shrimp promoters include promoters for the shrimp hyperglycemic hormone-like neuropeptide, shrimp vitellogenin, and kuruma shrimp actin (Gu and Chan 1998; Gu and Chan 1998; Tsang, Quackenbush et al. 2003). Additionally, promoters from other crustaceans can be used, such as the molt-inhibiting hormone (MIH) promoter from a crab (shown to be active when transfected into insect cell culture (Chan, Chen et al. 1998)) or the Actin 403 promoter from *Artemia franciscana* (Casero and Sastre 2001). Insect viral promoters, such as the polyhedron (polh) or p10 promoters of insect baculovirus (e.g., AcNPV), or insect promoters similar or equivalent to those in crustaceans (e.g., promoters for hemocyanin, MIH, actin, and etc.) can also be used. The molt inhibiting hormone, vittelogenin, hyperglycemic hormone-like neuropeptide, actin, actin 403, and hemocyanin are highly expressed genes. Therefore, their promoters can be advantageously used according to the present invention.

Examples of crustaceans that can express a recombinant infectious virus include, but are not limited to, shrimp, lobster, *Artemia,* crayfish, prawn, and crab. An infected crustacean or rotifer can be fed to a human or non-human animal. These animals can be produced in aquaculture or terrestrial agriculture. They include fish, shellfish, finfish, catfish, salmon and shrimp, as well as pigs, chickens, and cattle. They include all developmental stages of the animal, such as a larvae (in the case of an aquatic animal), juvenile, and adult.

In this embodiment, the crustacean or rotifer can be infected with a virus that is derived, synthetically or naturally, from a crustacean or rotifer virus.

Thus, in embodiments, the invention provides recombinant viruses. It provides DNA viruses, for example, White Spot Syndrome Virus, *Baculovirus penaei,* Infectious Hypodermal and Hemopoetic Necrosis virus, Hepatopancreatic Parvovirus, Spawner-isolated mortality virus, Lymphoidal Parvo-like Virus, MBV-type Penaeus monodon-type baculoviruses, Baculoviral midgut gland necrosis type viruses, type C *Baculovirus*, hemocyte-infecting non-occluded baculo-like virus, Systemic ectodermal and mesodermal baculo-like viruses, Rod Shaped Virus of *M. japonicus,* Penaeid acute viremia virus, Hypodermal and hematopoietic necrosis baculo-like virus, Shrimp Explosive Epidermic Disease agent, White Spot Baculo-like virus, Penaeid Rod-shaped DNA Virus, and Shrimp Iridovirus as well as other DNA viruses. The selection of a particular DNA virus can be made by those practicing the invention based on the particular crustacean or rotifer used and the particular protein or polypeptide to be expressed.

The invention provides RNA viruses, for example, Taura Syndrome Virus, reo-like virus type II, reo-like virus type IV, lymphoid organ vacuolization virus, rhabdovirus of penaid shrimp, yellow head virus, gill associated virus, and lymphoid organs virus, as well as other RNA viruses. The selection of a particular RNA virus can be made by those practicing the invention based on the particular crustacean or rotifer used and the particular protein or peptide to be expressed.

Furthermore, the recombinant virus can encode an exogenous protein expressed as a fusion protein. It can also encode an exogenous protein expressed with other proteins in a single operon. The virus can encode an antibody, an antibody fragment, a virus-like particle, a hormone, and/or a vaccine. The virus can also encode one or more anti-microbial compounds, including, but not limited to, cecropins, penaeidins, bactenecins, callinectins, myticins, tachyplesins, clavanins, misgurins, pleurocidins, parasins, histones, acidic proteins, and lysozymes.

Another embodiment provides the recombinant infectious virus, capable of infecting and replicating in a crustacean or rotifer cell, and includes a promoter active in that crustacean or rotifer, and a gene for a polypeptide that is not native to that virus. The virus can be either a DNA or an RNA virus.

The recombinant infectious virus of the invention can comprise a crustacean or rotifer promoter. For example, the promoter can be one that drives the expression of genes that are expressed at high levels, including, but not limited to, the molt inhibiting hormone, vittelogenin, hyperglycemic hormone-like neuropeptide, actin, actin 403, and hemocyanin. The infectious virus can also comprise an insect promoter or a viral promoter, i.e., a promoter typically used by an insect or virus. For example, the viral promoter can be the polyhedron promoter of *Baculovirus,* or the P3 promoter of IHHNV.

Yet another embodiment provides a method of producing a recombinant polypeptide, comprising infecting a crustacean and/or rotifer with a recombinant infectious virus that does not change the host cell genome, at a temperature permissive for infection, and which does not trigger viral injury. This virus replicates in one or more of the crustacean or rotifer cells. The temperature is then dropped to trigger increased viral replication and concurrent recombinant polypeptide expression. Crustaceans suitable for practicing this method include shrimp, *Artemia,* crawfish, lobster, and crab. The recombinant virus can be DNA or an RNA virus, e.g., WSSV, WSSV-related viruses, TSV, and/or TSV-related viruses. The temperature permissive for infection is at or above about 30° C., and the trigger temperature is at or below about 28° C.

Practicing this method can encompass consuming the entire crustacean or rotifer by a human or a non-human animal. The crustacean or rotifer can be processed before it is consumed. The recombinant polypeptide can be an antibody, an antibody fragment, a virus-like particle, a hormone, and/or a vaccine.

A further embodiment provides a method of delivering a therapeutic protein to a crustacean or rotifer by providing a recombinant, infectious virus to the crustacean or rotifer under conditions where the virus is internalized in the crustacean or rotifer, and the protein is present in the virus or produced by the virus upon internalization in the crustacean or rotifer. In this embodiment, the source of the virus can be, but is not limited to, a supernatant of cultured cells infected with the virus, or a crustacean or rotifer biomass infected with the virus.

Yet a further embodiment provides a method of producing an antigen in a crustacean or rotifer by infecting the crustacean or rotifer with a recombinant infectious virus comprising genetic material that expresses the antigen. Suitable crustaceans include shrimp, *Artemia,* lobster, crayfish, prawn, and crab. The recombinant infectious virus can be either a DNA or an RNA virus. Practicing this method can include purifying, or partially purifying, the recombinant infectious virus before infecting the crustacean or rotifer.

Another embodiment provides a method of vaccinating a human or non-human animal. Examples of animals for which vaccines of this embodiment can be produced include, but are not limited to, companion animals (e.g., dogs and cats), performance animals (e.g., horses and dogs), agricultural animals (e.g., cows, sheep, pigs, and chickens), aquatic animals (e.g., fish, crustaceans, and mollusks), and humans. The vaccine can be administered orally, e.g., as a part of the animal's feed, mucosally, e.g., nasally, by injection, e.g., intradermally or intravenously, or by other conventional methods. Vaccine titers can be determined by standard methods, such as ELISA; a typical titer is in the range of approximately 10-20 mg/g dry powder. A single oral dose for a human is in the range of approximately 1 mg vaccine protein. Adjustments in dosage for other animals, and other routes of administration can be made as is conventional in the art.

In order to produce the vaccine, the therapeutic protein or peptide is produced by infecting a crustacean or rotifer with a recombinant infectious virus, and providing the crustacean or rotifer to a human or non-human animal in an amount sufficient to elicit a protective immune response. The virus can be either a DNA or a RNA virus. The invention provides a method of production of a recombinant protein, such as a therapeutic protein, using a "temperature trigger" to synchronize the production of the recombinant protein. The host system can be initially infected at a high temperature, after which the production phase is triggered by a temperature drop, at which time all the infected crustaceans, e.g., shrimp, *Artemia,* lobster, crayfish, or crab, or rotifers, will synchronously begin producing virus and/or recombinant protein. This method significantly improves production efficiency by minimizing the effect of the recombinant protein production on cell growth until a high level, or even maximal, production can be achieved. Additionally, it might provide a mechanism to produce proteins that would otherwise be toxic to the organism.

A further embodiment involves a pill, capsule, patch, emulsion or suspension comprising a crustacean or rotifer, or parts thereof, which is infected by a recombinant virus containing a promoter that is active in that crustacean or rotifer and a gene for a protein not native to that virus.

Another embodiment provides a method of treating a human or non-human animal in need of such treatment by infecting a crustacean or rotifer with a recombinant infectious virus comprising one or more therapeutic protein, peptide, antibody, antibody fragment, virus-like particle, hormone, and/or vaccine, and further comprising a promoter that functions in the crustacean or rotifer to allow expression of the therapeutic protein; and contacting the human or non-human animal with the crustacean or rotifer. According to this embodiment, the method can be used to deliver insulin orally, mucosally, transdermally, and/or by injection. According to this embodiment, the therapeutic protein, peptide, antibody, antibody fragment, virus-like particle, hormone, and/or vaccine can inhibit the growth or replication of a bacterium, e.g., Vibrio, or a disease-causing virus, e.g., Taura virus or White Spot virus. The recombinant infectious virus can encode more than one polypeptide.

EXAMPLES

Certain embodiments of the invention will now be described in more detail through the following examples. The examples are intended solely to aid in more fully describing selected embodiments of the invention and should not be considered to limit the scope of the invention in any way.

Example 1

Production of Recombinant WSSV (rWSSV) With a Viral Promoter Driving Expression of a Selectable Marker The first step in the production of the rWSSV was to identify a region in the genome of the virus into which the gene of interest, with its accompanying promoter, can be inserted without affecting the infectivity of the virus itself. A particularly preferred site is an intergenic region of at least 200 base pairs, a known restriction site in a roughly central position, and possibly including a sequence that would not extensively overlap with an ORF. WSSV has two intergenic regions that are 400-460 bp in length—between Region 65-66 and Region 165-166 (van Hulten, Witteveldt et al. 2001). The intergenic region between ORF 65 and ORF 66 of the WSSV sequence as previously described (van Hulten, Witteveldt et al. 2001) was identified, amplified by PCR, and used as flanking regions around which the gene of interest, e.g., the selectable marker DsRed, BD Biosciences, is to be inserted.

The first half of the identified WSSV flanking region (FL1) was amplified using primers with engineered restriction sites NotI and SpeI at the 5' end to facilitate directional cloning downstream of the reporter gene DsRed. The FL1 was cloned downstream of the DsRed sequence in a pUC plasmid backbone, and transformed in *E. coli* subsequent PCR, restriction enzyme analysis, and sequence data confirmed its integrity.

The second half of the WSSV flanking region (FL2) was amplified using primers with engineered restriction sites SphI and XhoI. The FL2 was then directionally cloned upstream of the polyhedron (polh) promoter of the commercially available pFastBacDual plasmid (Invitrogen). The transformation was performed in *E. coli* and subsequent PCR, restriction enzyme analysis, and sequence data confirmed its integrity.

Finally, the DsRed/FL2 sequence was cut out of the pUC plasmid backbone using the appropriate restriction enzymes such as (BamHI and SpeI) and inserted downstream of the polh promoter in pFastBacDual plasmid. The final construct is shown in FIG. 1.

This final vector containing the polh promoter and the selectable marker between flanking sequences isolated directly from the intergenic regions of WSSV is then combined with native WSSV and used to co-infect whole shrimp or any cell culture susceptible to WSSV such as, but not limited to, shrimp primary cell cultures (Chen and Wang 1999). Cells expressing the rWSSV are identified by the appearance of the selectable marker—a red fluorescence. Cells or sectors displaying the selectable marker will represent the infectious rWSSV carrying the DsRed gene. These cells or tissues are excised and the rWSSV isolated and used to infect naive shrimp or a new primary shrimp cell culture to amplify the recombinant virus.

Example 2

Production of Recombinant WSSV with a Crustacean Promoter Driving Expression of a Selectable Marker A rWSSV can be produced using the procedures similar to those described in Example 1 with the following modifications. Larger flanking regions (800 bp) were chosen from sequences that include ORFs that have no homology to known proteins. These include the sequences around and including parts of ORF 65 and ORF 66 and are similarly designated FL1 and FL2. Furthermore, the p10 promoter present in pFastBacDual is used to express the foreign gene. In this case, FL1 and DsRed would be cloned upstream of the actin promoter and FL2 would be cloned downstream.

Example 3

Production of Recombinant WSSV with a Crustacean Promoter Driving Expression of a Selectable Marker The procedures described in Example 1 are followed, but rather than the polh promoter, a crustacean promoter is used. A particularly preferred promoter would be one that is highly expressed at all times such as, but not limited to, the promoter for a hemocyanin gene (e.g., Genebank accession #AF249297) or a beta-actin gene (e.g., Genebank accession #AF300705). Another preferred promoter would be one that can be regulated to induce expression by external means such as, but not limited to, a molt inhibition hormone gene (e.g., Genebank accession #AF092945). The sequences for these highly expressed genes are well known and the upstream promoter sequences can be easily obtained using standard molecular biology procedures. In this example, the upstream promoter region for the hemocyanin gene is used. The sequence of the Hemocyanin Promoter is amplified by PCR and substituted directly for the polh promoter as in Example 1. Following procedures laid out in Example 1, a rWSSV is produced which uses the shrimp promoter to drive expression of DsRed.

Example 4

Production of Recombinant IHHNV with an Insect or Viral Promoter Driving Expression of a Selectable Marker About 95% of the sequence of IHHNV is known and has been published (Shike, Dhar et al. 2000). IHHNV has a very small genome (3,873 nucleotides) relative to WSSV. Therefore, the insertion points of a gene of interest are more limited. As in WSSV, preferred sequences to be used as flanking elements will be intergenic regions that do not disrupt ORFs. There are at least two potential regions for gene insertion— one upstream of the left ORF and the other downstream of the right ORF. Using the same principle as outlined in Example 1, the first step in the production of the recombinant IHHNV is to prepare the sequence that will be used to recombine with the native virus. In this example, DsRed is again used as a selectable marker, as in the other examples, but other markers such as fluorescent proteins (e.g., green fluorescent protein (GFP), red fluorescent protein (RFP), yellow fluorescent protein (YFP), and other color variants), beta glucuronidase (GUS), antibiotic susceptibility (e.g., chloroamphenicol acyl transferase; CAT) and luciferase (e.g., lux and luc genes) can also be used.

Alternatively, to obtain a larger flanking sequence of IHHNV, the flanking regions can be extended on one side into the ORF in such a way that the ORF is not disrupted upon recombination. Additionally, and optionally, a native promoter of IHHNV (e.g., p2 or p61 promoter) is used to drive the DsRed reporter gene.

Example 5

Production of Recombinant TSV (rTSV) with a Viral Promoter Driving Expression of a Selectable Marker TSV is a 10.4 kb RNA virus and the full sequence has been published (Mari, Lightner et al. 2000; Robles-Sikisaka, Garcia et al. 2001). The first step in using TSV is to create an infectious clone. Vakharia and co-workers have created a full-length clone of a fish virus (IPNV) and have demonstrated that this full-length clone is infectious when applied to fish cells in culture (Yao and Vakharia 1998). Following the procedures described by Vakharia and colleagues, a full-length infectious clone of TSV can be produced. TSV has a very small genome relative to WSSV. Therefore, the potential insertion points for a gene of interest are more limited. As in WSSV, preferred sequences to be used as flanking elements will be intergenic regions that do not disrupt ORFs. With an infectious clone, there is no need for recombination with a native TSV and the molecular manipulations can be made to the infectious clone directly.

In this example, DsRed is again used as a selectable marker, but other markers, as described in Example 4, can also be used. The infectious clone of TSV is modified by the insertion of the P2-promoter of IHHNV and DsRed in the construct following the procedures described in Example 1. This construct is inserted in an intergenic region between two ORFs. The resulting recombinant infectious clone is used to infect whole shrimp or shrimp cell primary culture for amplification of the recombinant virus.

Example 6

Production of a Recombinant Sindbis Virus (rSV) with a Viral Promoter Driving Expression of a Selectable Marker Several viruses, including baculovirus and sindbis virus, have been shown to infect *Artemia* (Lewis, DeCamillis et al. 1999). *Artemia* (brine shrimp) are crustaceans that are particularly easy to culture and would represent a useful production system. The entire 12 kb sequence of Sindbis virus has been published (Strauss, Rice et al. 1984). The preparation of the recombinant Sindbis virus parallels somewhat the production methodology outlined in Example 1 for WSSV. Self replicating vector RNA molecules (replicons) are prepared with the gene of interest (e.g., Ds-Red) driven by a viral promoter by replacing internal genes as described by Xiang (Xiang, Lewis et al. 1989). This vector is used for transformation of the wild type Sindbis virus as described in Example 1 for WSSV and the recombinant virus is selected by the expression of the DsRed marker.

Example 7

Production of Recombinant *Baculovirus* (rBP) with a Viral Promoter Driving Expression of a Selectable Marker

*Baculovirus penaei* (BP) is a baculovirus that specifically attacks crustaceans (Brock, Lightner et al. 1983). Although the full sequence of this baculovirus is not known at this time, there are not many homologies with the known sequence of the baculoviruses that infect insects. Starting with the native virus, DNA is prepared using standard procedures and restriction enzymes (e.g., BamHI) is used to cut the sequence into pieces of approximately 1 kb. These restriction fragments are then sequenced to identify intergenic fragments that can be used as flanking regions around which a gene of interest is inserted. The selectable marker to be used will be Green Fluorescent Protein (GFP) although other selectable markers can also be used (see Example 4). Following the procedures outlined in Example 1, a construct is prepared in which the polh promoter and GFP are positioned with one half of the BP flanking region upstream of the polh promoter and the other half of the BP flanking region downstream of the GFP coding sequence. This construct is then combined with native BP and used to co-infect whole shrimp or shrimp cells from primary cell culture. Cells or sectors displaying the selectable marker will represent the infectious rBP carrying the GFP gene. These cells or tissues will be excised and used to infect naive shrimp or a new primary shrimp cell culture to amplify the recombinant virus.

Example 8

Production of Norwalk Vaccine in a Shrimp Using a Recombinant WSSV

Arntzen and colleagues (Tacket, Mason et al. 2000) have demonstrated that the expression of the one viral coat protein of Norwalk Virus (NV) in transgenic plants results in self-assembly into virus-like particles (VLPs). VLPs are empty, nonpathogenic particles that can effectively stimulate the immune system. The production of a recombinant vaccine for NV will use the methodology of Example 1 with the following exceptions. The construct that is added to the native WSSV for co-infection and selection of the rWSSV will consist of the polh promoter and the DsRed coding sequence (as in Example 1), but with the one viral coat protein gene inserted between the polh promoter and the DsRed gene. Both genes can be inserted in tandem to be read off as a single mRNA and driven by the same promoter. Retaining the selectable marker provides a method to identify and amplify the rWSSV carrying the NV vaccine. Once the rWSSV is amplified the expression of the DsRed gene can be knocked out, if desired, by a second-generation modification of the rWSSV. In this case, a construct prepared with the DsRed sequence will be modified to include a stop codon early in the sequence. This construct is co-transfected with the rWSSV and the newly modified rWSSV is selected from diseased shrimp that do not express the red color.

A biosecure shrimp production raceway (52 m$^2$) is prepared and stocked, as has been previously described for the shrimp production industry (Leung and Moss 2000; Pruder, Moss et al. 2001). Shrimp are grown to approximately 20-25 g in size over the next 90 days with a water temperature of about 32° C. Approximately 100 shrimp are removed to a holding tank and infected with the rWSSV by feeding of a small quantity of infected shrimp while the temperature is lowered to 25° C. Over the next 4-5 days, dead shrimp are collected, chopped into approximately 1 g pieces, and added back to the raceway. When all the infected shrimp have been utilized as feed, thereby infecting the entire raceway, the temperature of the raceway is lowered to 25° C. to trigger a massive infection of the shrimp. After about 4 days, shrimp are removed from the raceway, quick frozen, and stored until the vaccine is prepared.

NV vaccine is prepared by freeze-drying the shrimp and pulverizing the tissue into a fine powder. The vaccine titer is then determined using standard methods, such as ELISA-based colorimetric assays. A typical titer is in the range of approximately 10-20 mg/g dry powder. Based on the effective oral dosing data for NV vaccine prepared in transgenic plants (Tacket, Mason et al. 2000), approximately 1 mg of NV vaccine would constitute a single oral dose for a 60 kg human. Using standard binders for the production of tablets, 250 mg tablets are prepared containing approximately 1 mg of active vaccine. At a titer of 10 mg/g dry shrimp powder, the tablet mixture will be composed of 100 mg shrimp powder plus 150 mg of binder. Then 250 mg tablets are pressed according to standard procedures well known in the art.

Example 9

Production of Norwalk Vaccine in a Shrimp Using a Recombinant WSSV With Two Promoters Norwalk vaccine is produced in shrimp using a recombinant WSSV according to the procedure of Example 8 with the following exceptions. The gene coding for the viral coat protein is inserted into the pFastBacDual2 plasmid under control of the p10 promoter while the expression of the DsRed remains under the control of the polh promoter. Alternatively, the Norwalk viral coat protein gene can be inserted under the control of a second polh promoter engineered into the pFastBacDual2 downstream from the polh promoter controlling the DsRed as described in Example 1.

Example 10

Production of Lysin in *Artemia* using a Recombinant Sindbis Virus

The preparation of the recombinant Sindbis virus parallels that of Example 6 except the gene for the bacteriophage protein Lysin is inserted in the replicon instead of the selectable marker (e.g., Accession #NC_004112). Self replicating vector RNA molecules (replicons) are prepared with the gene for the Lysin protein driven by a viral promoter by replacing internal genes as described by Xiang (Xiang, Lewis et al. 1989). This vector is used for transformation of the wild type Sindbis virus as described in Example 1 for WSSV.

Example 11

Production of Lysin in Rotifers using a Recombinant Sindbis Virus

The preparation of the recombinant Sindbis virus parallels that of Example 6 except the gene for the bacteriophage protein Lysin is inserted in the replicon instead of the selectable marker (e.g., Accession #NC_004112). Self replicating vector RNA molecules (replicons) are prepared with the gene for the Lysin protein driven by a viral promoter by replacing internal genes as described by Xiang (Xiang, Lewis et al. 1989). This vector is used for transformation of the wild type Sindbis virus as described in Example 12 for WSSV.

Example 12

Production of an Antibody in a Shrimp Using a Recombinant WSSV

Antibodies are produced using the shrimp transfection system as described in Example 8 with the following modifications. Rather than the gene coding for the NV coat protein, genes are inserted coding for the heavy chain and the light chain of an antibody of choice. The transfection and production procedures are the same as described in Example 8 up to the stage of harvesting and freezing the infected shrimp. The frozen, infected shrimp containing the antibody are added to 10 parts by weight cold PBS (phosphate buffered saline; pH 7.2) containing protease inhibitors and homogenized at 5° C. The tissue is then filtered and washed several times with cold PBS to remove all the soluble protein. The filtrate is further centrifuged for additional clarification.

The soluble protein fraction containing the antibody can be used directly as a crude antibody preparation (ca. 10% of the total soluble protein) or further purified by methods well known to those in the art. One particularly preferable purification procedure is affinity binding wherein the antibody's substrate is bound to a particle (e.g., bound to a magnetic particle where the beads are added directly to the crude preparation then separated by a magnet). Particles binding the antibody are removed from the mixture and the purified antibody released by ionic, pH, or free substrate displacement.

Example 13

Production of Insulin in a Shrimp Using a Recombinant IHHNV

Flanking elements containing intergenic regions that do not disrupt ORFs are chosen as in Example 4. Using the same principle as outlined in Example 1, the first step in the production of the recombinant IHHNV is to prepare the sequence that will be used to recombine with the native virus. In this example, DsRed is replaced by the gene for insulin. Alternatively, to obtain a larger flanking sequence of IHHNV, the flanking regions can be extended on one side into the ORF in such a way that the ORF is not disrupted upon recombination. Additionally, and optionally, a native promoter of IHHNV (e.g., p2 and p61 promoter) is used to drive the DsRed reporter gene.

Example 14

Production of Erythropoietin in a Shrimp Using a Recombinant WSSV

Biopharmaceutical proteins, such as Erythropoietin (EPO), are produced using the shrimp transfection system as described in Example 8 with the following exceptions. Rather than the gene coding for the NV coat proteins, the EPO gene is inserted after the polh promoter. The transfection and production scheme is similar to that described in Example 9 through the stage of harvesting and freezing the infected shrimp up to the preparation of the crude soluble protein fraction. The soluble protein fraction containing the EPO can be used directly as a crude therapeutic preparation (ca. 10% of the total soluble protein) or further purified by methods well known to those in the art. One particularly preferable purification procedure would be an affinity binding procedure wherein an EPO antibody is bound to a particle (as described in Example 12) and added directly to the crude preparation. Particles binding the antibody are removed from the mixture and the purified EPO released by ionic, pH, or free substrate displacement.

Example 15

Production of Butylcholinesterase in an *Artemia* Using a Recombinant Sindbis Virus The preparation of the recombinant Sindbis virus parallels that of examples 6, 10, and 11 except the gene for the enzyme butrylcholinesterase (e.g., Accession #AF002993) is inserted in the replicon instead of the selectable marker. Self replicating vector RNA molecules (replicons) are prepared with the gene for the butrylcholinesterase protein driven by a viral promoter by replacing internal genes as described by Xiang (Xiang, Lewis et al. 1989). This vector is used for transformation of the wild type Sindbis virus as described in Example 1 for WSSV.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, as defined in the following claims.

REFERENCES

The following references are cited herein. The entire disclosure of each reference is relied upon and incorporated by reference herein.

1. Archer, D. B. and J. F. Peberdy (1997). "The molecular biology of secreted enzyme production by fungi." *Crit. Rev. Biotechnol.* 17(4): 273-306.

2. Brock, J. A., D. V. Lightner, et al. (1983). "A review of four viruses (BP, MBV, BMN, and IHNV) diseases of penaeid shrimp with particular reference to clinical significance, diagnosis and control in shrimp aquaculture." *Proc. 71st Intern Council for the Exploration of the Sea* Gen 10: 1-18.
3. Casero, M. C. and L. Sastre (2001). "Characterization of a functional serum response element in the Actin403 gene promoter from the crustacean *Artemia franciscana*." *Eur. J. Biochem.* 268(9): 2587-92.
4. Cereghino, G. P. and J. M. Cregg (1999). "Applications of yeast in biotechnology: protein production and genetic analysis." *Curr. Opin. Biotechnol.* 10(5): 422-7.
5. Cha, H. J., N. G. Dalal, et al. (1999). "Insect larval expression process is optimized by generating fusions with green fluorescent protein." *Biotechnol. Bioeng.* 65(3): 316-24.
6. Chan, S. M., X. G. Chen, et al. (1998). "PCR cloning and expression of the molt-inhibiting hormone gene for the crab (*Charybdis feriatus*)." *Gene* 224(1-2): 23-33.
7. Chen, S. N. and C. S. Wang (1999). "Establishment of cell culture systems from penaeid shrimp and their susceptibility to white spot disease and yellow head viruses." *Methods in Cell Sci.* 21: 199-206.
8. Compere, P., M. F. Jaspar-Versali, et al. (2002). "Glycoproteins from the cuticle of the Atlantic shore crab *Carcinus maenas*: I. Electrophoresis and Western-blot analysis by use of lectins." *Biol. Bull.* 202(1): 61-73.
9. Deutschen, M. P. (1990). "Guide to Protein Production." *Methods in Enzymology* 182.
10. Goosen, M. F. (1993). "Insect cell culture engineering: an overview." *Bioprocess Technol.* 17: 1-16.
11. Gu, P. L. and S. M. Chan (1998). "Cloning of a cDNA encoding a putative molt-inhibiting hormone from the eyestalk of the sand shrimp *Metapenaeus ensis*." *Mol. Mar. Biol. Biotechnol.* 7(3): 214-20.
12. Gu, P. L. and S. M. Chan (1998). "The shrimp hyperglycemic hormone-like neuropeptide is encoded by multiple copies of genes arranged in a cluster." *FEBS Lett.* 441(3): 397-403.
13. Keranen, S. and M. Penttila (1995). "Production of recombinant proteins in the filamentous fungus *Trichoderma reesei*." *Curr. Opin. Biotechnol.* 6(5): 534-7.
14. Leung, P. S. and S. M. Moss (2000). *Economic Assessment of a Prototype Biosecure Shrimp Growout Facility.* Controlled and Biosecure Production Systems: Evolution and Integration of Shrimp and Chicken Production Models., Sidney, Australia, World Aquaculture Society.
15. Lewis, D. L., M. A. DeCamillis, et al. (1999). "Ectopic gene expression and homeotic transformations in arthropods using recombinant Sindbis viruses." *Curr. Biol.* 9(22): 1279-87.
16. Mari, J., D. Lightner, et al. (2000). Full nucleotide sequence and genome organization of the Taura syndrome virus of Penaeid shrimp, GENBANK.
17. Montgomery-Brock, D., R. Y. Shimojo, et al. (2002). "The reduced impact of Taura Syndrome Virus on *Litopenaeus vannamei* juveniles held under hyperthermic conditions." *Center for Tropical and Sub-tropical Aguaculture—Regional Notes* 13:1-3.
18. Pruder, G. D., S. M. Moss, et al. (2001). Biosecure zero-exchange system for maturation and growout of marine animals U.S. Pat. No. 06,327,996
19. Ratledge, C. and B. Kristiansen (2001). *Basic Biotechnology*, Cambridge University Press.
20. Robles-Sikisaka, R., D. K. Garcia, et al. (2001). "Nucleotide sequence of 3'-end of the genome of Taura syndrome virus of shrimp suggests that it is related to insect picornaviruses." *Arch. Virol.* 146(5): 941-52.
21. Sambrook, J., E. Fritsch, et al. (1989). *Molecular Cloning: A Laboratory Manual.* Cold Spring Harbor, Cold Spring Harbor Press.
22. Scopes, R. K. (1984). *Protein Production,* Springer Verlag.
23. Shike, H., A. K. Dhar, et al. (2000). "Infectious hypodermal and hematopoietic necrosis virus of shrimp is related to mosquito brevidensoviruses." *Virology* 277(1): 167-77.
24. Stoger, E., M. Sack, et al. (2002). "Plantibodies: applications, advantages and bottlenecks." *Curr. Opin. Biotechnol.* 13(2): 161-6.
25. Strauss, E. G., C. M. Rice, et al. (1984). "Complete nucleotide sequence of the genome RNA of Sindbis virus." *Virology* 133: 42-110.
26. Tacket, C. O., H. S. Mason, et al. (2000). "Human immune responses to a novel norwalk virus vaccine delivered in transgenic potatoes." *J. Infect. Dis.* 182(1): 302-5.
27. Tsang, W. S., L. S. Quackenbush, et al. (2003). "Organization of the shrimp vitellogenin gene: evidence of multiple genes and tissue specific expression by the ovary and hepatopancreas." *Gene* 303: 99-109.
28. van Hulten, M. C., J. Witteveldt, et al. (2001). "The white spot syndrome virus DNA genome sequence." *Virology* 286(1): 7-22.
29. Vidal, O. M., C. B. Granja, et al. (2001). "A profound effect of hyphertheria on survival of *Litopenaeus vannamei* juveniles infected with White Spot Syndrome Virus." *J. World Aguaculture Soc.* 32: 364-372.
30. Xiang, C., R. Lewis, et al. (1989). "Sindbis virus: an efficient broad host range vector for gene expression in animal cells." *Science* 243: 1188-1191.
31. Yao, K. and V. N. Vakharia (1998). "Generation of infectious pancreatic necrosis virus from cloned cDNA." *J. Virol.* 72(11): 8913-20.

The invention claimed is:

1. A shrimp comprising a cell transfected with a recombinant virulent infectious virus selected from the group consisting of White Spot Syndrome Virus (WSSV) and Taura Syndrome Virus (TSV), wherein the virus does not change the genome of the shrimp, wherein the virus comprises a promoter operably linked to a gene that encodes a polypeptide that is not native to the virus, wherein virulence of the recombinant virulent infectious virus is temperature controllable, and wherein the infection by the recombinant virus is achieved at a high temperature that is permissive for such infection and then the temperature is lowered to trigger expression of the polypeptide that is not native to the virus.

2. The shrimp of claim 1, wherein the promoter comprises a promoter selected from a crustacean promoter or a viral promoter.

3. The shrimp of claim 1, wherein the recombinant virus comprises at least one promoter which is exogenous to the virus.

4. The shrimp of claim 1, wherein the polypeptide is, or is part of, a fusion polypeptide.

5. The shrimp of claim 1, wherein the polypeptide is expressed with other polypeptides in a single operon.

6. The shrimp of claim 1, wherein the virus encodes an antimicrobial polypeptide.

7. The shrimp of claim 1, wherein the virus encodes a polypeptide selected from an antibody, an antibody fragment, a viral polypeptide, a hormone, or a vaccine.

8. The shrimp of claim 1, wherein the cell is infected with the recombinant infected with the recombinant infectious virus at or above about 30 degrees Celsius, and wherein the expression of the polypeptide that is not native to the virus is triggered at or below 28 degrees Celsius.

9. A shrimp cell transfected with a recombinant infectious virus selected from the group consisting of White Spot Syndrome Virus (WSSV) and Taura Syndrome Virus (TSV), wherein the virus does not change the genome of the shrimp cell, wherein the virus comprises a promoter operably linked to a gene encoding a vaccine polypeptide that is not native to the virus, and wherein the virulence of the recombinant infectious virus is temperature controllable and wherein the infection by the recombinant virus is achieved at a higher temperature that is permissive for such infection and then the temperature is lowered to trigger expression of the polypeptide that is not native to the virus.

10. The shrimp cell of claim 9, wherein the promoter is a viral promoter.

11. The shrimp cell of claim 9, wherein the recombinant virus comprises at least one promoter which is exogenous to the virus.

12. The shrimp cell of claim 9, wherein the recombinant virus is an RNA virus.

13. The shrimp cell of claim 9, wherein the polypeptide comprises a fusion polypeptide or a fragment thereof.

14. The shrimp cell of claim 9, wherein the polypeptide is expressed with other polypeptides in a single operon.

15. The shrimp cell of claim 9, wherein the shrimp cell is infected with the recombinant infectious virus at or above about 30 degrees Celsius, and wherein the expression of the polypeptide that is not native to the virus is triggered at or below about 28 degrees Celsius.

* * * * *